US005470748A

United States Patent [19]
Hayden et al.

[11] Patent Number: 5,470,748
[45] Date of Patent: Nov. 28, 1995

[54] METHOD FOR MEASURING THE RELATIVE CATALYTIC ACTIVITY OF CARBONACEOUS CHARS

[75] Inventors: Richard A. Hayden; Thomas M. Matviya, both of Pittsburgh, Pa.

[73] Assignee: Calgon Carbon Corporation, Pittsburgh, Pa.

[21] Appl. No.: 266,137

[22] Filed: Jun. 27, 1994

Related U.S. Application Data

[63] Continuation-in-part of Ser. No. 6,470, Jan. 21, 1993, abandoned.

[51] Int. Cl.$^6$ ............................ G01N 31/10; G01N 25/20
[52] U.S. Cl. .................. 436/37; 436/147; 422/51
[58] Field of Search ........................... 436/37, 127, 147, 436/135; 422/51; 73/190 R, 191

[56] References Cited

U.S. PATENT DOCUMENTS

| | | | |
|---|---|---|---|
| 3,726,644 | 4/1973 | Desnoyers et al. | 436/147 X |
| 3,740,194 | 6/1973 | Hendy | 422/51 X |
| 4,130,016 | 12/1978 | Walker | 73/190 R |
| 4,208,907 | 6/1980 | Townsend et al. | 73/190 R |
| 4,963,499 | 10/1990 | Stockton et al. | 436/137 |

OTHER PUBLICATIONS

Nelson Smith et al. "Carbon–Catalyzed Decomposition of Hydrogen Peroxide," Faraday Society Transactions, 62(CA):2553–65/1966.

Primary Examiner—James C. Housel
Assistant Examiner—Harold Y. Pyon
Attorney, Agent, or Firm—Titus & McConomy

[57] ABSTRACT

A method is provided for evaluating the catalytic activity of carbonaceous chars via the decomposition of hydrogen peroxide in contact with such materials. In this method the rise in temperature occasioned by the decomposition of hydrogen peroxide under essentially adiabatic conditions is monitored as a function of time. By use of this method, carbonaceous chars having high catalytic activities may be rapidly and conveniently identified.

12 Claims, 1 Drawing Sheet

5,470,748

METHOD FOR MEASURING THE RELATIVE CATALYTIC ACTIVITY OF CARBONACEOUS CHARS

CROSS-REFERENCE

This is a continuation-in-part of U.S. patent application Ser. No. 08/006,470 filed Jan. 21, 1993, now abandoned, entitled Method for Measuring Catalytic Activity of Carbonaceous Char.

FIELD OF THE INVENTION

The present invention relates to a test method and to a peroxide test method for the evaluation of the catalytic activity of carbonaceous chars by means of their reaction with hydrogen peroxide.

BACKGROUND OF THE INVENTION

No standardized test for determining the catalytic activity of materials such as activated carbons and chars has been reported. It has been known that carbonaceous chars such as activated carbons have the ability to decompose aqueous solutions of hydrogen peroxide. Tests using this reaction can be used to distinguish chars having different chemical and physical characteristics. These prior art peroxide tests typically involved the use of isothermal volumetric techniques wherein the rate of oxygen evolution was measured for a carbon/peroxide system at constant temperature. These techniques are generally expensive, tedious, and time-consuming, requiring a reasonably sophisticated apparatus to permit reaction of the carbon with the peroxide and measurement of the rate of gas evolution at constant temperature.

An alternative test is to measure the rate of the reaction at a given temperature using calorimetric techniques. However, such tests are sophisticated and require great attention to detail to produce meaningful results. Moreover, because of the difficulty in producing meaningful results and achieving reproducibility, such tests have not been generally recognized as a standardized methodology for rating the catalytic activity of carbonaceous chars.

Accordingly, it is the object of the present invention to provide a test for the measurement of the relative catalytic properties of carbonaceous chars which is inexpensive, simple, flexible, and convenient, and provides meaningful indications of catalytic activity in a relatively short period of time. It is a further objective to provide a test method capable of functioning as a standardized, reproducible methodology.

SUMMARY OF THE INVENTION

Generally, the present invention provides a method for establishing an index by which the relative catalytic activities of carbonaceous chars can be evaluated. The index is derived by measuring the time required to achieve a certain fraction of the maximum contact of a carbonaceous char with a material which decomposes exothermically and catalytically upon such contact. In particular, the method of the present invention provides for the rapid evaluation of the relative catalytic activity of carbonaceous chars by contacting a defined amount of a material, such as peroxide, especially, hydrogen peroxide or a peroxide-like material in aqueous solutions with a defined amount of a carbonaceous char. The rise in system temperature resulting from the heat evolved by the ensuing decomposition of the peroxide is monitored as a function of time. This temperature rise is monitored in any convenient manner until the reaction is complete as indicated by the cessation of both heat generation and the corresponding temperature rise of the system. The index is then established by determining the time required for this temperature rise to achieve a predetermined fraction, preferably three-fourths, of the maximum temperature rise. This time is used as an index to compare the relative catalytic activities of other carbonaceous chars the indices of which are determined in the same manner.

In contrast to known art, the present invention does not require the careful measurement of evolved gas volumes or residual hydrogen peroxide, or maintenance of the system under essentially isothermal conditions. Likewise, repeated small additions of hydrogen peroxide that result in only slight perturbations to the system temperature are not required. Most importantly, it provides a useful, repeatable method for comparing the relative catalytic activity of various chars.

In a preferred embodiment of the invention, the carbonaceous char is first pulverized to a very fine mesh size fraction. Typically, this pulverization is found to be satisfactory if greater than 90% by weight of the char will pass through a 325 mesh U.S. Standard Series sieve. Other particle size distributions may be used but diffusional and other effects may severely bias the results. Once pulverized, a defined portion of the carbonaceous char is placed into the sample chamber of the test apparatus. The size of this defined portion of the carbonaceous char is best stipulated on a mass basis, and should be selected such that the rate of decomposition of the defined amount of hydrogen peroxide proceeds at a conveniently measurable rate which enables accurate and precise determinations of the reaction mixture temperature as a function of time.

Once placed into a sample chamber, the pulverized carbonaceous char is wetted with a defined quantity of buffer solution. The volume of the buffer solution is such that the carbonaceous char is freely suspended in the solution once mechanical mixing is initiated. The mixing speed should be sufficient not only to suspend the pulverized carbonaceous char but also to minimize any bulk diffusion effects on the rate of hydrogen peroxide decomposition. Bulk diffusion effects are minimized by use of a mixing speed such that additional increases in the mixing speed do not result in significant increases in the rate of peroxide decomposition. Generally, mixing speeds that result in the formation of a significant vortex in the mixture are adequate.

The buffering capacity of the buffer solution is selected such that the reaction mixture is maintained at the desired pH irrespective of the pH-related effects of the carbonaceous char and/or the hydrogen peroxide solution and/or the reaction products thereof. The buffer solution is most conveniently aqueous in nature although non-aqueous solutions may also be used. The preferred pH of the buffer solution is seven (neutral). A higher or lower pH buffer solution may be used, but it should be realized that the rate of peroxide decomposition is pH dependent. As such, a change in pH of the buffer solution may be used to change the range of the test. Any liquid may be substituted for the buffer solution but a loss of buffering capacity may result. This loss of buffering capacity must be compensated for if it occurs.

After the addition of the buffer solution to the char, mechanical stirring of the mixture and monitoring of the temperature of the carbonaceous char-buffer solution mixture are initiated. Once this mixture has achieved a constant, preferably ambient temperature, a defined amount of hydrogen peroxide is rapidly added to the stirring mixture. Preferably, the hydrogen peroxide is in an aqueous solution of defined volume at a temperature equal to that of the carbonaceous char-buffer solution mixture. The quantities of either solution that are adequate to satisfy the requirements of this test are not critical provided that sufficient materials are available to result in an accurate, measurable system temperature increase with respect to time. Non-aqueous solutions of hydrogen peroxide may be used provided these solutions are miscible with the buffer solution and also wet the carbonaceous char without occluding the catalytic sites responsible for decomposition of the peroxide. Other types of peroxides may be used neat or in solution depending on the characteristics of the individual peroxide. But, the safety and convenience of dilute hydrogen peroxide aqueous solutions make them the preferred peroxide reactants in the present invention.

The temperature of the reaction mixture is monitored until the temperature increases to a constant value. For a given reaction mixture and adiabatic apparatus the magnitude of this temperature increase is essentially independent of the catalytic activity of the carbonaceous char. However, the rate at which this maximum temperature is achieved is dependent on the catalytic properties of the carbonaceous char. Therefore, for a given reaction mixture, the elapsed time required for the system to achieve the maximum temperature, or some portion thereof, can be used to quantitatively compare the catalytic activities of a variety of carbonaceous chars. Typically, the approach of the system temperature to this maximum value is initially very fast but becomes relatively slow once 80 to 90% of the maximum temperature has been achieved. Therefore, an increase in precision and accuracy is obtained by comparing the elapsed times required for carbonaceous chars to achieve some percentage less than about 80% of the total temperature rise. In the present invention, this value has been selected as 75%, i.e., the time required for the reaction mixture to achieve three-quarters of the total temperature rise possible. This value of this elapsed time period is referred to as the "t-¾ time". This value is typically expressed in units of minutes. The lower the t-¾ time, the higher is the level of catalytic activity for a given char. Thus, the "t-¾ time" is used to quantitatively evaluate and subsequently rank the catalytic activities of carbonaceous chars. Typical values of the t-¾ time for commercial activated carbons are in excess of 30 minutes.

Other advantages of the present invention will become apparent from a perusal of the presently preferred embodiments of the invention taken in connection with the accompanying drawing.

PRESENTLY PREFERRED EMBODIMENTS

Figure 1:
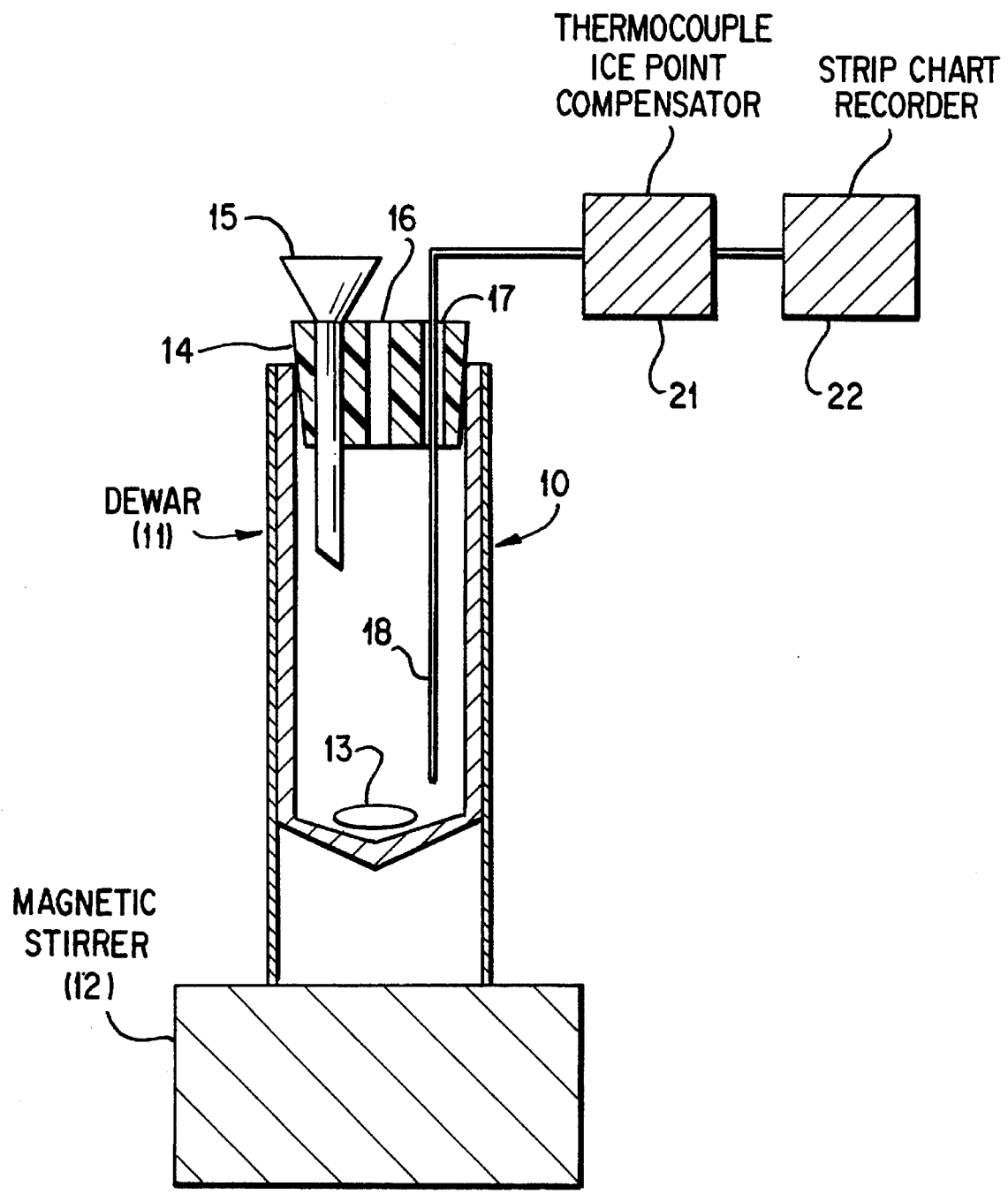
FIG. 1 is a diagrammatic view of a representative apparatus for conducting the tests according to the method of the present invention.

The following examples illustrate the preferred embodiment of the present invention. In these examples, carbonaceous chars are prepared by several different processes known in the art. With reference to FIG. 1, an apparatus 10 is shown which is useful in conducting the tests of the present invention. Apparatus 10 includes a Dewar 11 (Catalog Number 10-195A, Fisher Scientific, Pittsburgh Penn., or functionally equivalent) positioned on a magnetic stirrer 12 (Model PC-35 1, Corning Hot Plate Stirrer, Corning Scientific Products, Corning, N.Y., or Model 18425 Nuova II Stir Plate, Thermolyne Corporation, Dubuque Iowa, or functionally equivalent) and containing therein a magnetic stir bar 13. A beveled, tightly fitting, closed-cell styrofoam cap 14 is positioned in the top of Dewar 11 and includes a funnel 15, a vent 16 and an opening 17 there through and into Dewar 11. Through opening 17 is positioned thermocouple 18 which is electrically connected to ice point compensator 21 and strip chart recorder 22. All of the subsequent tests were performed using apparatus 10.

EXAMPLE 1

WPL-L, a commercially available activated carbon (Calgon Carbon Corporation, Pittsburgh Pa.) was sized to produce an approximately less than 12 mesh size and greater than 20 mesh size (U.S. Standard Series sieves) material.

Portions of this material were heated to 900° C. in a small rotary kiln under an inert gas flow. Once the desired 900° C. temperature was achieved, the inert gas flow was stopped and a mixture of ammonia gas and water vapor having a molar ratio of 0.4 moles NH3 to 1.0 moles H2O was injected into the kiln. These conditions were maintained for differing periods of time, after which the treated carbonaceous chars were cooled to ambient temperature under an inert gas flow. Two carbonaceous char samples produced in this manner exhibited Apparent Densities (Test Method TM-7, Calgon Carbon Corporation, Pittsburgh Pa.) of 0.606 grams per cc and 0.541 grams per cc.

The catalytic activities of these samples were determined by measuring the time required for each to decompose a given quantity of aqueous hydrogen peroxide. In practice, the carbonaceous char to be tested is first pulverized such that greater than 90% of the material would pass through a 325 mesh U.S. Standard Series sieve. The styrofoam cap 14 of dewar 11 is removed and a 0.250 gram portion of this pulverized material is placed therein. Deionized water (100 mL) is then added to the Dewar. The addition of this water is performed in such a manner that any pulverized carbonaceous char clinging to the sides of Dewar 11 is carried into the main body of the water in the bottom. Next, a 50 mL aliquot of aqueous buffer solution is added to the Dewar. This buffer solution is 0.50 molar in $K_2JPO_4$ and 0.50 molar in $KH_2PO_4$. At this point magnetic stir bar 13 is placed into the Dewar and the magnetic stirrer is energized. Stirring speed is increased until a vortex greater than about ½" deep is formed in the mixture and the optimum stirring speed is achieved. The optimum stirring speed is selected such that additional increases in stirring speed do not significantly affect the peroxide decomposition time. Once identified, this optimum stirring speed can be used for all subsequent char samples. If the stir bar 13 decouples from the magnetic field before the optimum stirring speed is achieved, it is replaced with a bar which couples more strongly with the magnetic field of the stirrer (12). Optionally, Dewar 11 can be replaced with an equivalent unit that, due to manufacturing variances, positions the stir bar farther into the magnetic field of the stirrer 12. If the stir bar still does not adequately couple with the magnetic field of the stirrer 12, the Dewar can be shortened by removing some of the bottom portion of the outside metal casing. Styrofoam cap 14 is now replaced, and thermocouple 18 (Type K or J, 1/16" diameter, Inconel sheathed, ungrounded, or functionally equivalent) is inserted through styrofoam cap 14 and into the mixture such that a measurement representative of the mixture temperature can be obtained, and the thermocouple ice point compensator 21 (Model MCJ-J or MCJ-K, Omega Engineering, Inc., Stamford, Conn. or functionally equivalent) and strip chart recorder 22 are energized.

The strip chart recorder tracing is monitored until the system is seen to come to thermal equilibrium at ambient temperature. Once thermal equilibrium is achieved, 50 mL of an aqueous hydrogen peroxide solution (0.42 moles H2O per 50 mL) is added, as rapidly as possible, to the Dewar through the funnel 15 in the styrofoam cap. Care is taken to ensure that the hydrogen peroxide solution is at ambient temperature prior to the addition. As the hydrogen peroxide solution is added to the Dewar, the strip chart recorder tracing is marked to indicate the time of addition. The strip chart recorder tracing is then monitored until the tracing indicates that a constant temperature above ambient has been reached. Using the materials and procedures described, this constant temperature is typically about 40° C. greater than ambient temperature. At this point, the styrofoam cap is removed from the Dewar and the action of the stir bar is observed.

If the stir bar is no longer mixing the solution in the desired manner the entire procedure is repeated. If adequate mixing is observed, the elapsed time required for the recorder tracing to reach 75% of its maximum deflection is determined. This value represents the time required for the catalytically active carbonaceous char to decompose three-fourths of the available hydrogen peroxide and is referred to as the t-¾ time. This value is reported in units of minutes. The catalytic activities (t-¾ times) of the carbonaceous chars described above, when determined using this method, are 11.4 minutes for the char exhibiting the 0.606 grams per cc Apparent Density and 6.2 minutes for the char exhibiting the 0.541 grams per cc Apparent Density.

EXAMPLE 2

WPL-L, a commercially available activated carbon (Calgon Carbon Corporation, Pittsburgh Pa.) was sized to produce an approximately less than 12 mesh size and greater than 20 mesh size (U.S. Standard Series sieves) material.

A portion of this material was heated to 950° C. in a small rotary kiln under an inert gas flow. Once the desired 950° C. temperature was achieved, the inert gas flow was stopped and a mixture of ammonia gas and water vapor having a molar ratio of 0.4 moles NH3 to 1.0 moles H2O was injected into the kiln. These conditions were maintained for 180 minutes, after which the treated carbonaceous char was cooled to ambient temperature under an inert gas flow. A char sample produced in this manner exhibited an Apparent Density (Test Method TM-7, Calgon Carbon Corporation, Pittsburgh Pa.) of 0.470 grams per cc. The catalytic activity of this sample was determined using the procedure given in Example 1. This carbonaceous char exhibited a t-¾ time of 8.6 minutes.

EXAMPLE 3

F300, a commercially available activated carbon (Calgon Carbon Corporation, Pittsburgh Pa.) was sized to produce an approximately less than 12 mesh size and greater than 20 mesh size (U.S. Standard Series sieves) material.

Portions of this material were heated to 950° C. in a small rotary kiln under an inert gas flow. Once the desired 950° C. temperature was achieved, the inert gas flow was stopped and a mixture of ammonia gas and water vapor having a molar ratio of 0.2 moles NH3 to 1.0 moles H2O was injected into the kiln. These conditions were maintained for differing periods of time, after which the treated carbonaceous chars were cooled to ambient temperature under an inert gas flow.

Two char samples produced in this manner exhibited Apparent Densities (Test Method TM-7, Calgon Carbon Corporation, Pittsburgh Pa.) of 0.392 grams per cc and 0.414 grams per cc. The catalytic activities of these chars were determined using the procedure given in Example 1. The catalytic activities (t-¾ times) of the carbonaceous chars described above were 3.7 minutes for the char exhibiting the 0.392 gram per cc Apparent Density and 6.9 minutes for the char exhibiting the 0.414 gram per cc Apparent Density.

EXAMPLE 4

F300, a commercially available activated carbon (Calgon Carbon Corporation, Pittsburgh Pa.) was sized to produce an approximately less than 12 mesh size and greater than 20 mesh size (U.S. Standard Series sieves) material. A portion of this material was mixed with water and nitric acid in the ratio of 125 grams of carbon to 1 liter of 12 molar nitric acid solution. This mixture was then heated to a temperature between 85° C. and 100° C. The mixture was maintained in this temperature range for about seven hours. At the end of this time period the mixture was cooled to ambient temperature. After cooling, the supernatant liquid was decanted and the carbonaceous char was extensively rinsed with water. The char was then dried in air at 125° C. A portion of this nitric acid-treated char was then placed into a small rotary kiln. A flow of ammonia gas was established into this kiln. At this point the kiln temperature was raised from ambient to 950° C. over a time period of about 1.5 hours. The kiln temperature was maintained at 950° C. for 30 minutes. Following this treatment, the ammonia flow to the kiln was stopped and a flow of inert gas to the kiln was initiated. The kiln was then cooled to ambient temperature at which time the flow of inert gas was stopped and the char was removed from the kiln. A carbonaceous char sample produced in this manner exhibited an Apparent Density (Test Method TM-7, Calgon Carbon Corporation, Pittsburgh Pa.) of 0.408 grams per cc. The catalytic activity of this sample was determined using the procedure given in Example 1. This char exhibited a t-¾ time of 4 minutes.

While presently preferred embodiments of the invention have been described in particularity, the invention may be otherwise embodied within the scope of the appended claims.

What is claimed:

1. A method for establishing an index of catalytic activity for a carbonaceous char for the purpose of comparing the relative catalytic activity between carbonaceous chars said method comprising:

(a) combining a carbonaceous char with a material that undergoes an exothermic reaction, said reaction being catalyzed by the presence of said char to provide a temperature rise;

(b) determining said temperature rise from initiation of said reaction by measuring temperature as a function of elapsed time from the initiation of said reaction to a maximum temperature of said reaction;

(c) establishing an index of catalytic activity for said carbonaceous chars by determining the minimum time required for said temperature rise to achieve a predetermined temperature which is less than or equal to said maximum temperature, wherein said minimum time to achieve temperature is said index of catalytic activity for said carbonaceous char.

2. The method of claim 1 wherein step(a) is conducted under adiabatic conditions.

3. The method of claim 1 wherein the said predetermined temperature is three-fourths of said maximum temperature.

4. The method of claim 1 wherein the ratio of the amount of said carbonaceous char to the amount of said material is the same for each carbonaceous char for which an index is to be established for comparison between such chars.

5. The method of claim 1 wherein said material is hydrogen peroxide.

6. The method of claim 1 wherein said reaction is carried out in liquid phase.

7. The method of claim 6 wherein the amount of said material is selected such that the liquid phase does not boil.

8. The method of claim 7 wherein said material is solubilized in said liquid phase prior to combination with said carbonaceous char.

9. The method of claim 7 wherein said carbonaceous char is wetted with, and suspended in, a liquid prior to said combining with said material.

10. The method of claim 6 wherein said liquid phase is aqueous.

11. The method of claim 9 wherein said liquid is aqueous.

12. The method of claim 11 wherein said carbonaceous char is wetted with, and suspended in, an aqueous pH buffer solution prior to and during said combining with said material.

* * * * *